United States Patent
Kingston et al.

(10) Patent No.: US 9,869,684 B2
(45) Date of Patent: Jan. 16, 2018

(54) ACCURATE MEASUREMENT OF GLUTATHIONE FOR DISEASE DIAGNOSIS AND DRUG METABOLITE SCREENING

(75) Inventors: Howard M. Kingston, Pittsburgh, PA (US); Mehmet Pamukcu, Sunnyvale, CA (US)

(73) Assignee: Definitek, Inc., Pittsburgh, PA (US)

( * ) Notice: Subject to any disclaimer, the term of this patent is extended or adjusted under 35 U.S.C. 154(b) by 939 days.

(21) Appl. No.: 13/530,769

(22) Filed: Jun. 22, 2012

(65) Prior Publication Data

US 2013/0158886 A1 Jun. 20, 2013

Related U.S. Application Data

(60) Provisional application No. 61/500,656, filed on Jun. 24, 2011.

(51) Int. Cl.
| | |
|---|---|
| *G01N 33/48* | (2006.01) |
| *G01N 33/50* | (2006.01) |
| *G01N 33/96* | (2006.01) |
| *G01N 33/487* | (2006.01) |
| *A61B 5/15* | (2006.01) |
| *A61B 10/00* | (2006.01) |
| *G06F 19/10* | (2011.01) |
| *G01N 33/68* | (2006.01) |

(52) U.S. Cl.
CPC ............ *G01N 33/96* (2013.01); *A61B 5/15* (2013.01); *A61B 10/00* (2013.01); *A61B 10/0051* (2013.01); *G01N 33/487* (2013.01); *G01N 33/68* (2013.01); *G06F 19/10* (2013.01)

(58) Field of Classification Search
None
See application file for complete search history.

(56) References Cited

U.S. PATENT DOCUMENTS

| | | | | |
|---|---|---|---|---|
| 5,414,259 | A * | 5/1995 | Kingston | ............... G01N 30/88 250/282 |
| 6,235,495 | B1 | 5/2001 | Fu et al. | |
| 2005/0287623 | A1 | 12/2005 | Yan et al. | |
| 2008/0014595 | A1 * | 1/2008 | Janssen-Heininger | G01N 33/58 435/7.1 |
| 2009/0029409 | A1 | 1/2009 | Soga et al. | |

OTHER PUBLICATIONS

James et al. Efficacy of methylcobalamin and folinic acid treatment on glutathione redox status in children and autism. THe American Journal of Clinical Nutrition, 2009, vol. 89, pp. 425-430.*
Johnson et al. A rapid LC-FTMS method for the analysis of cysteine, cystine and systeine/systine steady-state nredox potential in human plasma. Clinica Chimica Acta, vol. 396, 2008, pp. 43-48.*
Owen, Joshua B.. et al., "Measurement of oxidized/reduced glutathione ratio," Protein Misfolding and Cellular Stress in Disease and Aging: Concepts and Protocols, Methods in Molecular Biology, Springer Science+Business Media, LLC, 2010, vol. 648, pp. 269-277.
Iwasaki, Yusuke, et al, "Chromatographic and mass spectrometric analysis of glutathione in biological samples," Journal of Chromatography B, Oct. 15, 2009, vol. 887, No. 28, pp. 3309-3317.
Fahrenholz, Timothy, et al., "Molecular Speciated Isotope Dilution Mass . . . " Analytical Chemistry, 2015, 87, 1232-1240.
Melnyk, Stepan et al, "A new HPLC method . . . using coulometric electrochemical detection," J. Nutr. Biochem., 10:490-497, 1999.

* cited by examiner

*Primary Examiner* — Russell S Negin
(74) *Attorney, Agent, or Firm* — Barbara E. Johnson, Esq.

(57) ABSTRACT

A method of measuring and calculating (preferably by a computer with output to a user) tGSH (total glutathione very particularly defined) with sample preparation and assay methods that have been confirmed to provide accurate and reliable tGSH and related diagnostic assays in blood or tissue from a patient.

2 Claims, 8 Drawing Sheets

Figure 1:
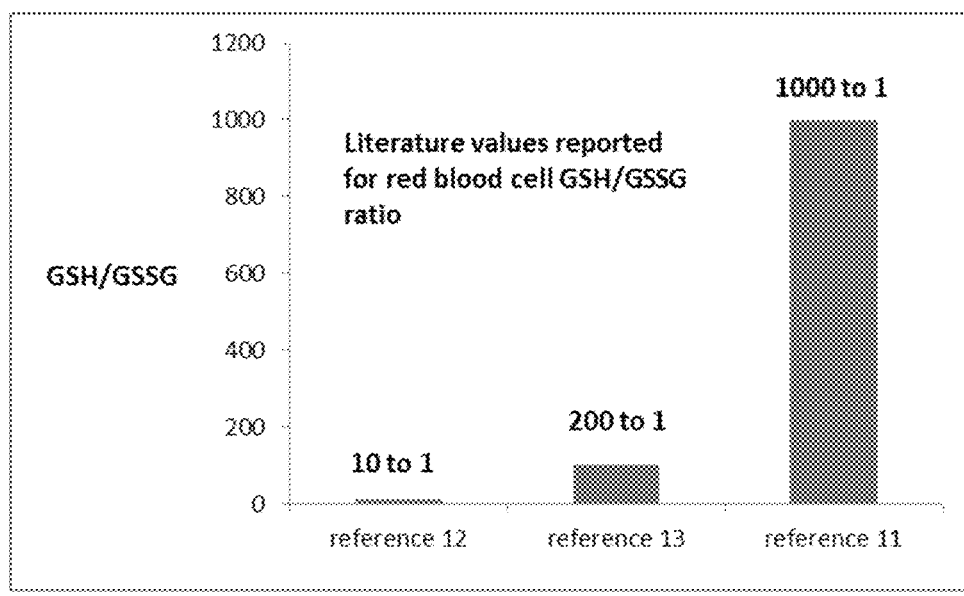

ACCURATE MEASUREMENT OF GLUTATHIONE FOR DISEASE DIAGNOSIS AND DRUG METABOLITE SCREENING

CROSS REFERENCE TO RELATED APPLICATIONS

This patent application claims priority to, and incorporates herein by reference, U.S. Provisional Patent Application No. 61/500,656 filed 24 Jun. 2011.

BACKGROUND OF THE INVENTION

Field of the Invention

Measurement of total Glutathione in blood and other body fluids and tissues must be accurate in order to have diagnostic significance or the ability to participate in drug metabolite screening.

Description of Related Art

Previously, glutathione deficiency was examined as a possible prognostic for survival in Acquired Immunodeficiency Syndrome (AIDS), as disclosed for example in U.S. Pat. No. 5,843,785. In that patent, general glutathione levels of whole blood and/or T-cells of HIV positive patients were determined (directly or indirectly) as an indication of the likely period of survival, as well as the need for agents for enhancing the glutathione levels. But the determination made was not accurate enough to make any kind of correlation with survival expectancy of HIV positive patients. Moreover, it was also mentioned "referring to glutathione levels, it will be understood that it is the value determined by an assay which can be used for comparisons, but does not provide an absolute value". Therefore since the glutathione determinations were not accurate and absolute, the stated hypothesis was not valid enough to corroborate probability of survival in HIV positive patients. The probability of survival expectancy of HIV positive patients does not depend on one particular biomolecule measurement such as glutathione, but on several other conditions associated with the etiology of the disease. The methods both (HPLC and FACS) used for the determination glutathione levels are not robust enough to address the problems associated with quantification like reduced glutathione oxidation, and conjugates formation.

Similarly, in Pastore, G. Federici, E. Bertini, F. Piemonte, "Analysis of glutathione: implication in redox and detoxification," *Clinical Chim Acta* 333 (2003) 19-39, blood concentrations of reduced glutathione (GSH) in various pathologic conditions, and the statistical significance of the purported validation one or more sub-species, are indicated as being diagnostically significant. Unfortunately, most if not all of the asserted data are not accurate, which presents a significant problem for physicians in assessing and treating patients. In many cases the imprecision of these GSH and GSSG numbers overlap as they are not compared with confidence intervals but with means which are not statistically different.

United States Published Patent Application No. US2011/0144205 A1 hypothesized that glutathione is a key biomarker for heart failure asymptomatic patients, stating that "inflammation and oxidative stress are key components of in the pathophysiology and progression of heart failure and are strongly associated with the disease severity." Chemically, oxidative stress is associated with increased production of oxidizing species or a significant decrease in the effectiveness of antioxidant defenses. Therefore, these antioxidant defenses can be not only glutathione but also can be vitamin E, vitamin C, enzymes like superoxide dismutase, metallothionein, etc. The method for quantification of glutathione mentioned is not accurate and precise enough to correct for glutathione oxidation and conjugate formations.

In "Methods for the Quantitation of Oxidized Glutathione," U.S. Pat. No. 6,235,495 B1, the method used for quantification of oxidized glutathione based on the assay developed by Tietze, which is based on spectrophotometric determination of the reaction of the Ellman's reagent with Glutathione disulfide. The observation is made by assessing the color at a particular absorbance. The invention mentioned in this patent is the use of 1-methyl-2-vinylpyridinium trifluromethanesulfonate (M2VP) to prevent the conversion of GSH to GSSG without interfering with glutathione reductase in the biological sample. However, this method is not accurate and precise enough to make since clinical and therapeutic decisions, it is based on the color change at particular absorbance and any other disulfide present in the biological sample can interfere with the process and can lead to false positive result.

The invention in the published U.S. Patent Application No. US2009/0029409 involves determination of oxidative stress biomarker, which can be varied by perturbation of glutathione levels in the blood. The oxidative stress biomarker candidate identified is ophthalmic acid, but the mechanism as to how glutathione is affected has not been established clearly. Although reduced glutathione is present in low concentrations and prone to oxidation in blood, it still can be quantified by using NEM in the sample preparation which minimizes the conversion of reduced glutathione to oxidized glutathione. The normal range of ophthalmic acid present in the blood has not been mentioned and whether its production is varied by any other biomolecule other glutathione has not been discussed.

Zhenying Yan and coinventors have described, in two US patents, 2005/US0287623 and 2011/US788186, a method for detecting reactive metabolites by isotope trapping with a mass spectrometer for the purpose of toxicological assessment. In both Yan patents, the European patent by Michael J. Avery (EP, 1,150,120, October 2001) has been provided as a prior art that involves incubating a test compound with a microsomal drug metabolizing enzyme system in the presence of a form of glutathione and then, detecting certain glutathione adducts formed therefrom using tandem mass spectrometry. Yan points out that Avery method will identify reactive metabolites as well as non-reactive components (including both unreactive metabolites and components of the reaction mixture) formed as a result of common response in mass spectrometry detection, thus resulting in false positives. In the 2005-Yan patent, a method of detecting reactive metabolites of a drug candidate whereby the drug candidate was mixed with a non-labeled trapping agent, an isotopically labeled trapping agent and an enzyme. Purportedly improving on the 2005-patent, Yan and Norman D Huebert, U.S. Pat. No. 7,884,186 B2, disclosed in the 2011 text that the 2005-patent detects only "soft" metabolites, but does not simultaneously detect both "hard" and "soft" reactive metabolites. In the 2011 Yan specification, the "soft" metabolite is described as any electrophilic metabolite which comprise at least one substituent group which readily reacts with soft electrophiles, such as the sulfhydryl group in cysteine and the —SH group on the compound of the formula. Disclosed examples of soft metabolites were given as quinones, quinone imines, immunoquinone, methids, epoxides, arene oxides and nitrenium ions. The same patent described a hard metabolite as an electrophilic metabolite which comprises at least one substitute group which readily reacts with the —(CH$_2$)$_4$—NH$_2$ of the compound of the formula. The disclosed example of such substituent group was given as aldehydes. Additionally, the same patent claims that its isotope trapping technique was capable of eliminating false positives using mass spectrometric pattern recognition. There is no indisputable evidence in either of the Yan patents that would support the claims associated with the "elimination of false positives." Without standard reference materials, a mathematical basis and statistical support, such claims would not meet the criteria established for mission critical applications such as those established in the clinical, diagnostic and homeland security fields.

In the above exemplary prior art, the field attempts to identify various glutathione adducts and conjugates has therefore been fraught with fundamental problems. A need remains, therefore, for an accurate method of measuring and calculating tGSH and specific related compounds and conjugates in a patient's blood, fluid or tissue sample and the concomitant diagnostic method of interpreting the measurements and ratios for diagnostic and prognostic purposes. A need also remains for improved accuracy in situ toxicological drug screening of biologic drugs involving GSH, GSH species, GSH conjugates, and GSH metabolites.

SUMMARY OF THE INVENTION

In order to meet this need, the present invention is a method of measuring and calculating (by a computer with output to a user) tGSH (total glutathione very particularly defined) with sample preparation and assay methods that have been confirmed to provide reliable tGSH and related diagnostic assays in blood or tissue from a patient. Moreover, the method of accurate measurement and calculation of tGSH, GSH (reduced glutathione) and the ratio of GSH to oxidized glutathione (GSSG) has enabled for the first time the identification of the diagnostic range of the ratio of GSH/GSSG as 15-200, wherein a human having a ratio within the range 15-200 is vulnerable to disease including but not limited to autism and chronic fatigue syndrome. An increase in this ratio over treatment time for a patient indicates positive response to therapy—up to maximum ratio values of about 600-800 for healthy individuals. In particular, after accurate measurement and calculation according to this specification, a tGSH concentration of 2.8-3.0 micromoles tGSH per gram of blood is prognostic of autism in children and young adults, and a GSH level of 2.2-2.4 micromoles per gram of blood is prognostic of autism in children and young adults. The measurements are conducted using speciated isotope dilution mass spectrometry to assess particular variants (reduced, oxidized, conjugated, etc.) of glutathione and the calculations are preferably conducted automatically, following mass spectrometry, to provide readouts of tGSH, GSH and the ratio of GSH/GSSG using the following equations, where tGSH is the sum of GSH$_{corrected}$, GSSG$_{corrected}$ and CGSH, and the ratio is given by:

$$\frac{GSH}{GSSG} = \frac{z}{\gamma}$$

where:

$$z = GSH_{corrected} = GSH_{SIDMS} + \alpha + \beta$$

$$\alpha = \left[ GSH \xrightarrow{oxidation} GSSG \right]$$

-continued $$\beta = CGSH = \sum_i CGSH_1 + CGSH_2 + \ldots CGSH_i$$

$$\gamma = GSSG_{corrected} \left( GSSG - \left[ GSH \xrightarrow{oxidation} GSSG \right] \right)$$

The mass spectrometry measurements and calculations are preferably performed using a computer and the results are presented as an output to a user, usually a printout on paper or a readout on a computer screen, showing values for tGSH, GSH and the ratio of GSH/GSSG.

BRIEF DESCRIPTION OF THE DRAWING(S)

Figure 2:
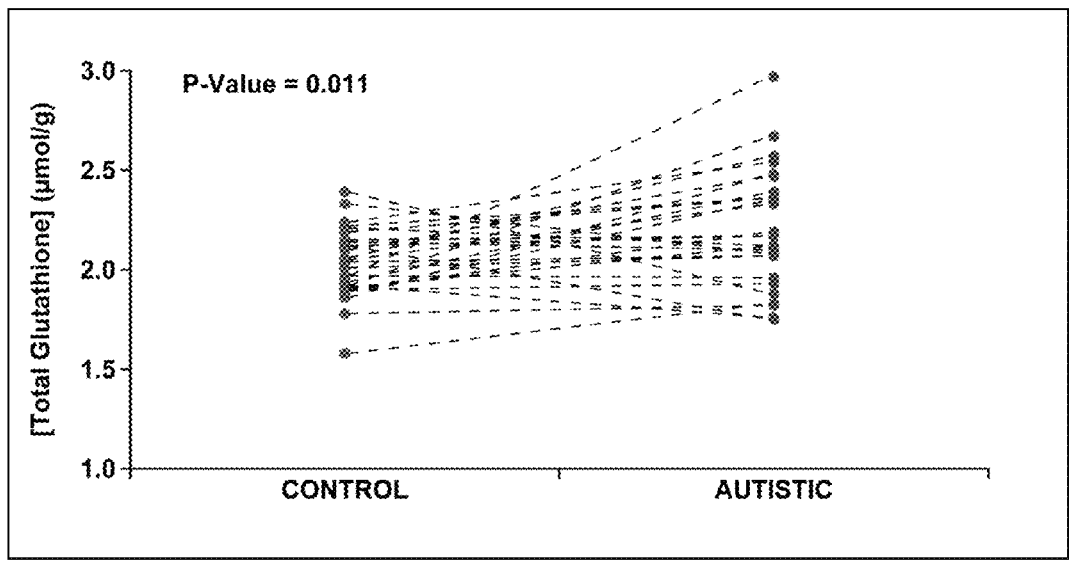

FIG. 1: A bar graph showing prior art literature values for ratio of total glutathione to reduced glutathione;

FIG. 2: A line graph showing average red blood cell tGSH according to the invention, in children with autism and controls. The p value is 0.011 with n=27 pairs.

Figure 3:
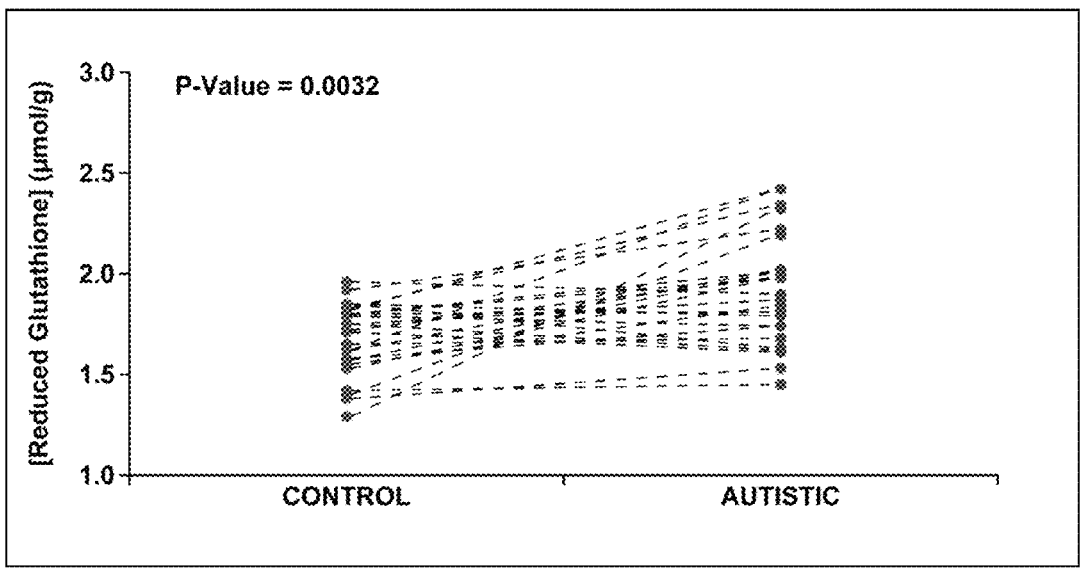

FIG. 3: A line graph showing mean red blood cell GSH concentrations in children with autism and controls. For n=25 pairs, the results are significant with a p value of 0.0032.

Figure 4:
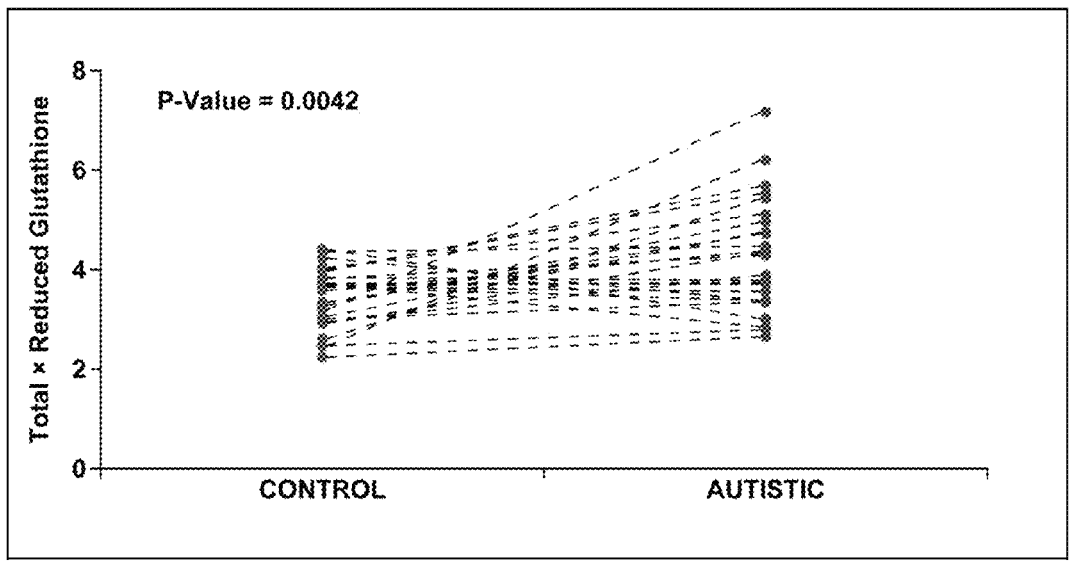

FIG. 4: A line graph showing red blood cell tGSH concentration times red blood cell GSH in children with autism and controls. For n=25 pairs, the p value equals 0.0042.

Figure 5:
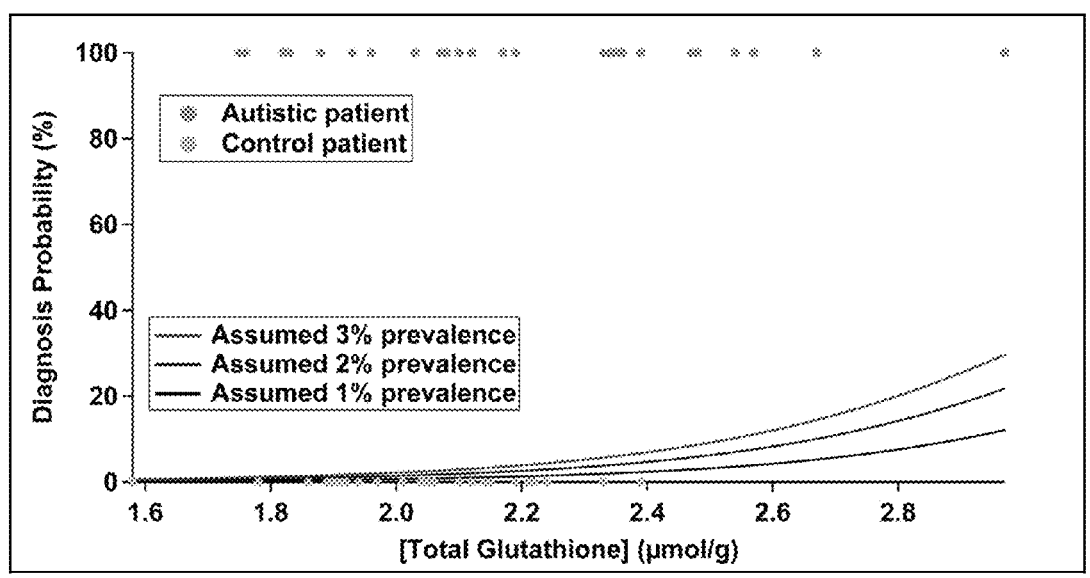

FIG. 5: A line graph showing logistic regression analysis of red blood cell tGSH concentration versus autism diagnosis probability for n=27 pairs.

Figure 6:
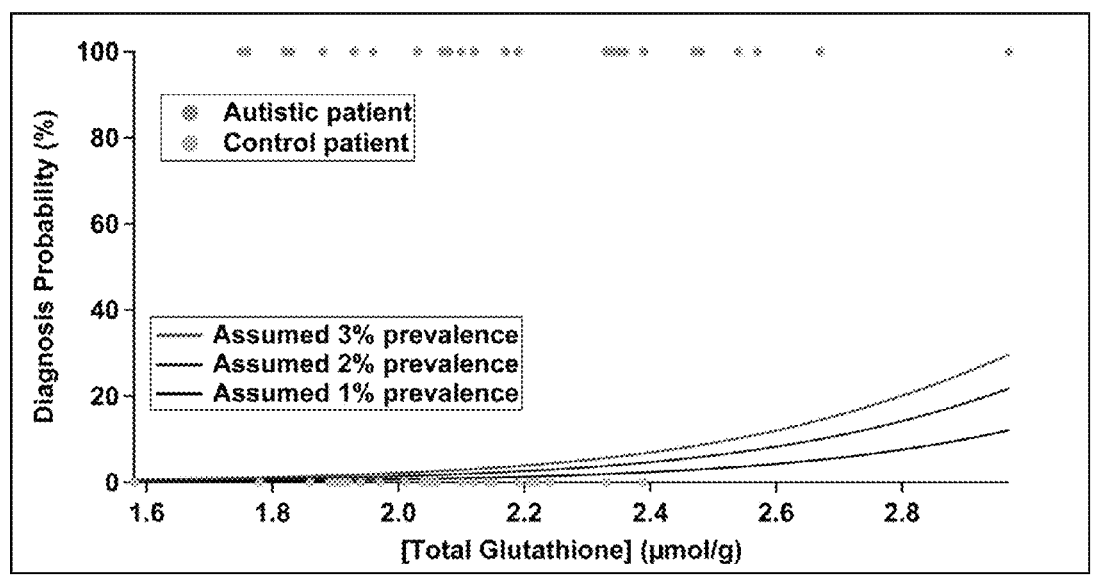

FIG. 6: A line graph showing Logistic regression analysis of red blood cell GSH concentration versus autism diagnosis probability for n=25 pairs.

Figure 7A:
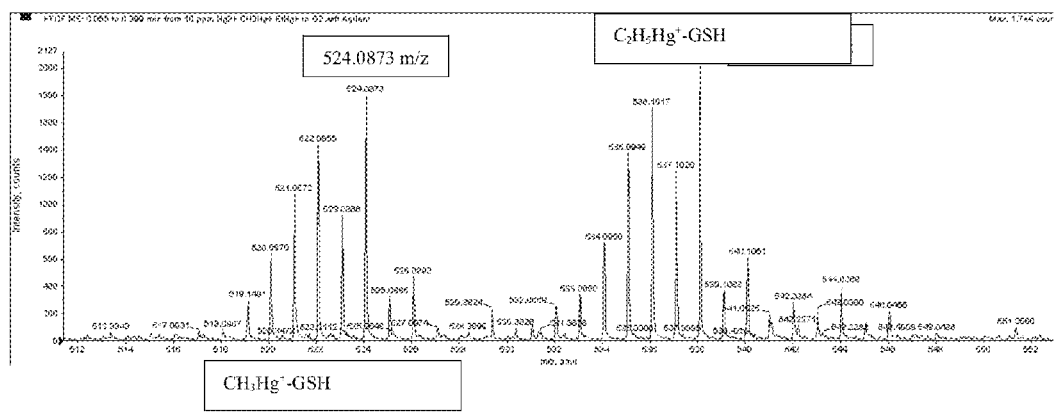
Figure 7B:
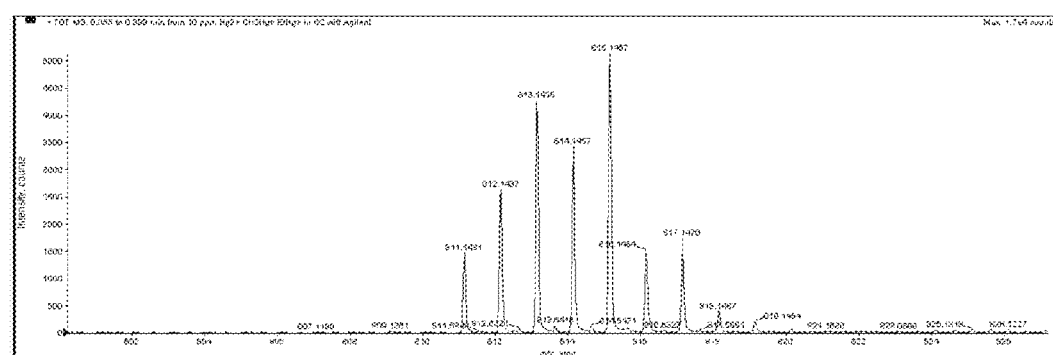

FIGS. 7a and 7b: Mass spectrometry printouts of simultaneous analysis of glutathione conjugated with three mercury species by D-SIDMS using nano-ESI-TOF-MS.

Figure 8:
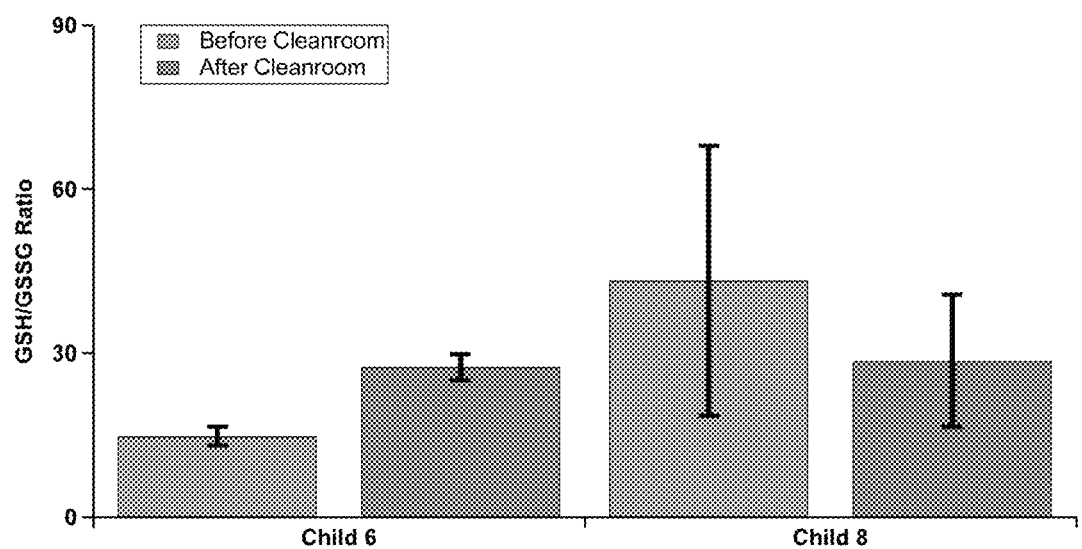

FIG. 8: A bar graph shows the GSH/GSSG corrected ratios of two young twin female ASD patients. The n is approximately 12 replicate measurements with 95% confidence limit.

DETAILED DESCRIPTION OF THE INVENTION

Quantitatively low, high, and quantifiable levels of reduced and oxidized glutathione species (GSH and GSSG, respectively) and conjugates of glutathione are diagnostic and prognostic of diseases including but not limited to immune system diseases and autism. The invention is a method of accurately and reliably assaying for particularly defined glutathione species levels, together with quantitative interpretation of the data for diagnostic significance. The method applies direct, mathematical, calibration-curve-free isotope dilution mass spectrometry (D-IDMS) accounting for species' transformations and conjugates, and achieving mass balance higher accuracy for actionable applications. The invention creates an accurate assessment of GSH, GSSG, conjugated GSH (CGSH), and GSH/GSSG ratio with corrections of transformations by direct IDMS (D-IDMS) or direct speciated isotope dilution mass spectrometry (D-SIDMS) accounting for the four forms of glutathione that are frequently referred to collectively and also quantified as GSH by most other methods, without the essential and diagnostically significant corrections taught herein.

Therefore, the present invention is a diagnostic and prognostic assay for glutathione species concentrations in the blood or other fluids and tissues or matter of an animal or human for which diagnosis or prognosis is indicated, comprising assaying a quantity of blood and/or blood components or other fluids such as urine and tissues or matter such as improved "GSH Assay" of drug conjugates with glutathione using special direct algorithmic speciated isotope dilution mass spectrometry (D-SIDMS) and algorithmic corrective evaluations. In some instances in Autism Spectrum of Diseases (ASD), the level of total Glutathione (tGSH) as defined herein is elevated. When blood is the sample for which assay analysis is conducted, tGSH is measured at approximately 2.8-3.0 and greater micromoles tGSH per gram blood, yielding a biochemical diagnoses that indicate a 15% onset probability for ASD. For reduced glutathione, or GSH as defined herein, 2.2 to 2.4 micromoles per gram concentration in blood, then a biochemical diagnosis of 40% probability of onset of ASD is indicated.

As a non-limiting example, a newborn baby blood test for ASD by accurate assessment of total glutathione and its related suite of tGSH, GSH, GSSG, CGSH and GSH/GSSG ratio in whole blood, red blood cells, serum, plasma, lymphatic fluid, cerebrospinal fluid, saliva, tears, urine, cells or tissues can identify those newborns that are at greatest risk for ASD and thus identify those candidates for early intervention by nutritional therapy and other therapeutic strategies.

Low glutathione levels as defined and disclosed herein are also diagnostic for diseases where immune system compromised or dysfunctional, such as without limitation the condition known as chronic fatigue syndrome, several forms of cancer and more than a dozen disease conditions where immune system is compromised.

The definition of the glutathione compounds and conjugates disclosed herein is extremely important. Therefore, the present invention a method of measuring and calculating (by a computer with output to a user) tGSH (total glutathione very particularly defined) with sample preparation and assay methods that have been confirmed to provide reliable tGSH and related diagnostic assays in blood or tissue from a patient. Moreover, the method of accurate measurement and calculation of tGSH, GSH (reduced glutathione) and the ratio of GSH to oxidized glutathione (GSSG) has enabled for the first time the identification of the diagnostic range of the ratio of GSH/GSSG as 15-200, wherein a human having a ratio within the range 15-200 is vulnerable to disease including but not limited to autism and chronic fatigue syndrome. An increase in this ratio over treatment time for a patient indicates positive response to therapy—up to maximum ratio values of about 600-800 for healthy individuals. In particular, after accurate measurement and calculation according to this specification, a tGSH concentration of 2.8-3.0 micromoles tGSH per gram of blood is prognostic of autism in children and young adults, and a GSH level of 2.2-2.4 micromoles per gram of blood is prognostic of autism in children and young adults. The measurements are conducted using speciated isotope dilution mass spectrometry to assess particular variants (reduced, oxidized, conjugated, etc.) of glutathione and the calculations are conducted automatically, following mass spectrometry, to provide readouts of tGSH, GSH and the ratio of GSH/GSSG using the following equations, where tGSH is the sum of $GSH_{corrected}$, $GSSG_{corrected}$ and CGSH, and the ratio is given by:

$$\frac{GSH}{GSSG} = \frac{z}{\gamma}$$

where:

$$z = GSH_{corrected} = GSH_{SIDMS} + \alpha + \beta$$

$$\alpha = \left[ GSH \xrightarrow{oxidation} GSSG \right]$$

$$\beta = CGSH = \sum_i CGSH_1 + CGSH_2 + \ldots CGSH_i$$

$$\gamma = GSSG_{corrected} \left( GSSG - \left[ GSH \xrightarrow{oxidation} GSSG \right] \right)$$

The mass spectrometry measurements and calculations are performed using a computer and the results are presented as an output to a user, usually a printout on paper or a readout on a computer screen, showing values for tGSH, GSH and the ratio of GSH/GSSG.

The present invention may be understood, therefore, to be a diagnostic and prognostic assay for glutathione concentration in blood or other tissue or matter of animals or human beings for which diagnosis or prognosis is indicated, comprising assaying a quantity of blood and/or other tissue or matter for glutathione constituent concentrations using D-SIDMS. High or low glutathione levels are also diagnostic for diseases of the compromised immune system or immune system dysfunction, such as without limitation the condition known as "chronic fatigue syndrome" and several types of cancer. There are at least twenty diseases in which accurate tGSH, GSSG, CGSH and corrected GSH/GSSG ratios are diagnostic biomarkers, but accurate measurements of these "species" has been impossible heretofore. These diseases include, without limitation, Autism, Breast cancer, Diseases requiring hemodialysis, Conditions requiring Enalapril treatment, AIDS, Ataxia telangiectasia, Lung cancer, Macular degeneration, Diabetes, Preeclampsia, Bile duct obstruction, Colon cancer (initial), Colon cancer (advanced), Coronary heart surgery, Retinopathy of prematurity, Preeclampsia, Diabetic preeclampsia, and Atherosclerosis.

As a nonlimiting example, a child's blood test for ASD by accurate assessment of tGSH as described herein can identify those children that are at greatest risk for ASD and thus identify those candidates for early intervention by nutritional, interventions, and physician supervised therapy.

While the diagnostic levels reported above are for blood levels of tGSH, the invention is also applicable as assays of animal or human tissue, fluids other than blood, or matter including but not limited to keratinaceous fingernail samples or hair. Diagnostic levels in tissues or matter other than blood must be extrapolated because they will vary proportionately from blood.

In addition to using D-IDMS to assay for tGSH, the invention embraces the speciation assay, with D-SIDMS, of any or all of tGSH, GSH, GSSG, or the GSH/GSSG ratio, along with optional concurrent assessment of concentration of conjugated toxins and toxicants, including but not limited to methylmercury, inorganic mercury, cadmium and lead.

Accurate and clinically relevant analyses of glutathione levels in patient samples, including blood, fluids, tissue or biological matter have been possible for the first time by implementing D-SIDMS. Previous assays for glutathione or GSSG have been highly inaccurate, unreliable and unsuitable for use as diagnostic or prognostic information. By "D-SIDMS" it is meant the technology described in the following U.S. patents and patent application documents, each of which is incorporated herein by reference: U.S. Pat.

No. 6,790,673 entitled, "Speciated isotope dilution mass spectrometry of reactive species and related methods;" U.S. Pat. No. 5,414,259 entitled, "Method of speciated isotope dilution mass spectrometry;" and U.S. patent application Ser. No. 11/952,471 entitled, "Solid phase and catalyzed enabled automated isotope dilution and speciated isotope dilution mass spectrometry."

D-IDMS and D-SIDMS techniques have been successfully applied for the analyses of tGSH, GSH and GSSG (glutathione disulfide) and obtain accurate concentration values for all three species, primarily on the bases of isotopic values of the natural abundant and enriched standards without using an external calibration curve. The techniques were used to measure one (by D-IDMS) or three (by D-SIDMS) of the species in the blood samples of autistic children and controls.

As shown in FIG. 1 and prior to the present invention, quantitation methods listed in the scientific literature involved creation of a calibration curve and serial dilution of a standard at different concentrations within the expected range of the analyte in the sample mixture. Quantitative analysis of GSH and its oxidized form, GSSG, although highly desirable as a key diagnostic biomarker, has not been reliably achieved by using external calibration, as evidenced by wide differences in reported tGSH/GSSG concentration values as shown in the PRIOR ART FIG. 1. Prior to tGSH analysis, traditional sample preparation typically involved treating disulfide bonds with a reducing agent, such as dithiothreitol (DTT). For analysis of GSH and GSSG, analytical methods have included LC separation with either fluorescence or mass spectrometry detection. A derivatization agent, such as NEM, is often used during sample preparation to block the thiol group on GSH, thereby minimizing its conversion to GSSG.

The D-SIDMS technique described in this specification includes spiking the sample with known amounts of the enriched analytes of interest (and pairs of related analytes), analyzing the sample by mass spectrometry, and determining concentrations and extent of species interconversion by analyzing analyte peak ratios. In other words, the optimized D-SIDMS technique involves spiking the sample with known amounts of the enriched analytes of interest (and pairs of related analytes), analyzing the sample by mass spectrometry, and determining concentrations and extent of species interconversion by analyzing analyte MS peak ratios.

An attempt to preserve a sample was discussed in a paper by others, in which the authors added NEM in the blood draw tube such that the formation of the GSH-NEM conjugate occurred in the tube immediately when the blood was drawn. The NEM significantly reduces GSH oxidation but does not stop it. By contrast, in this invention, isotopically enriched GSH and GSSG, along with the NEM, are added to the blood draw tube or other fluid or sample collection containers, thereby enabling use of D-SIDMS (US EPA Method 6800A). This approach allowed measurement and correction of GSH oxidation/conjugation, which typically occurs during shipment of a sample to the laboratory from a remote location, thereby enabling one to obtain samples for analysis from around the globe. This improved sample stabilization and spiking method for GSH/GSSG analysis such that, even if some GSH does convert to GSSG in the presence of NEM, the correct concentrations of both analytes can still be obtained because of the ability to correct for conversion of GSH to GSSG at the time of analysis in the laboratory.

Analysis of samples described in this invention were made using the mass spectrometer in positive mode, and the collision energy used for tandem MS purposes for the GSH-NEM complex (which resulted in the primary product ion being one with the loss of pyroglutamate) was 12V, and that for GSSG (resulting in the loss of two pyroglutamates) was 25V. The transitions monitored for the first 6.5 minutes were 433.1 m/z→304.1 m/z (for the most abundant isotope from the natural abundant GSH-NEM molecular ion), 434.1 m/z→305.1 m/z, 435.1 m/z→306.1 m/z, 436.1 m/z→307.1 m/z (for the most abundant isotope from the isotopically enriched GSH-NEM molecular ion), 437.1 m/z→308.1 m/z, 438.1 m/z→309.1 m/z, 439.1 m/z→310.1 m/z, 440.1 m/z→311.1 m/z, 441.1 m/z→312.1 m/z, 442.1 m/z→313.1 m/z, 443.1 m/z→314.1 m/z, 613.1 m/z→355.1 m/z (for the most abundant isotope from the natural abundant GSSG molecular ion), 614.1 m/z→356.1 m/z, 615.1 m/z→357.1 m/z, 616.1 m/z→358.1 m/z (for possible GSSG molecular ion resulting from combination of one natural abundant GSH and one enriched GSH), 617.1 m/z→359.1 m/z (for most abundant isotope from isotopically enriched GSSG molecular ion), 618.1 m/z→360.1 m/z, 619.1 m/z→361.1 m/z (for possible most abundant isotope from enriched GSSG from combination of two enriched GSH's), 620.1 m/z→362.1 m/z, 621.1 m/z→363.1 m/z, 622.1 m/z→364.1 m/z, 623.1 m/z→365.1 m/z, 624.1 m/z→366.1 m/z. The transitions monitored for the last 18.5 minutes were all of the ones for GSSG (613.1 m/z→355.1 m/z (for the most abundant isotope from the natural abundant GSSG molecular ion), 614.1 m/z→356.1 m/z, 615.1 m/z→357.1 m/z, 616.1 m/z→358.1 m/z (for possible GSSG molecular ion resulting from combination of one natural abundant GSH and one enriched GSH), 617.1 m/z→359.1 m/z (for most abundant isotope from isotopically enriched GSSG molecular ion), 618.1 m/z→360.1 m/z, 619.1 m/z→361.1 m/z (for possible most abundant isotope from enriched GSSG from combination of two enriched GSH's), 620.1 m/z→362.1 m/z, 621.1 m/z→363.1 m/z, 622.1 m/z→364.1 m/z, 623.1 m/z→365.1 m/z, 624.1 m/z→366.1 m/z). The resolving power used for both the first and third quadrupoles (MS1 and MS3) was what Agilent termed "unit" (peak width 0.7 amu at half height). The retention time for the GSH-NEM complex was ~3 minutes, and that for the GSSG was ~8 minutes. The capillary voltage was 3500V, and the fragmentor voltage was 135V. The dwell time was 50 ms for the first 6.5 minutes and 5 ms for the final 18.5 minutes. The autosampler tray was kept at 4° C.

The general equation for D-IDMS is shown below.

$$C_x = \left(\frac{C_s W_s}{W_x}\right)\left(\frac{A_s - R_m B_s}{R_m B_x - A_x}\right) \qquad \text{Formula 1}$$

In Formula 1, as shown above, $A_x$=abundance of isotope A in the natural abundant analyte in the sample; $B_x$=abundance of isotope B in the natural abundant analyte in the sample; $A_s$=abundance of isotope A in the enriched analyte in the spike; $B_s$=abundance of isotope B in the enriched analyte in the spike; $C_x$=concentration of the natural abundant analyte in the sample, which is what the equation is solving for $C_s$=concentration of enriched analyte in the spike in µmol/g; $W_x$=weight of the sample; $W_s$=weight of the spike; and $R_m$=measured ratio of isotope A to isotope B (obtained from the mass spectrometry measurements).

A sample calculation according to the previous Formula 1 is shown below as Table I:

TABLE I $A_x$ = abundance of 182.1 m/z product ion in the natural abundant GSH in the sample (0.00445)
$B_x$ = abundance of 179.1 m/z product ion in the natural abundant GSH in the sample (0.879)
$A_s$ = abundance of 182.1 m/z product ion in the enriched GSH in the spike (0.880)
$B_s$ = abundance of 179.1 product ion in the enriched GSH in the spike (0.00337)
$C_x$ = concentration of GSH in the sample (unknown)
$C_s$ = concentration of enriched GSH in the spike in µmol/g (2.31)
$W_x$ = weight of the sample (0.0198 g)
$W_s$ = weight of the spike (0.0222 g)
$R_m$ = measured ratio of 182.1 m/z product ion to 179.1 product ion (obtained from the mass spectrometry measurements) (1.07)
$C_x$ = [((2.31 µmol/g)(0.0222 g))/(0.0198 g)] × [((0.880) − (1.07 × 0.00337))/ ((1.07 × 0.879) − 0.00445)] = 2.42 µmol/g
Molecular weight of GSH = 307 µg/µmol
$C_x$ in µg/g (or ppm) = (2.42 µmol/g)(307 µg/µmol) = 742 ppm In describing the D-SIDMS equations for GSH and GSSG analysis that are designed to correct for conversion of GSH to GSSG, it is best to start off with a simple analogy. If one has several slices of wheat bread and several slices of white bread, one can make three types of sandwiches: ones with two slices of wheat bread, ones each with a slice of wheat bread and a slice of white bread ("hybrid" sandwiches), and ones with two slices of white bread. In a similar manner, if natural abundant GSH (307 g/mol) and isotopically enriched GSH with two $^{13}C$'s and one $^{15}N$ (310 g/mol) are equilibrated and oxidation occurs, one can end up with three types of oxidized GSSG: natural abundant GSSG (612 g/mol) from two molecules of natural abundant GSH (analogous to wheat bread sandwiches), partially enriched GSSG (615 g/mol) with two $^{13}C$'s and one $^{15}N$ from the combination of one natural abundant GSH molecule and one isotopically enriched GSH molecule (analogous to the "hybrid" sandwiches), and GSSG with four $^{13}C$'s and two $^{15}N$'s (618 g/mol) from two molecules of enriched GSH (analogous to the white bread sandwiches). One can then determine how much of the GSH converted to GSSG by spiking the sample with enriched GSSG in which the enrichment is different from the enriched GSSG that comes from oxidation (such as GSSG that has four $^{13}C$'s (616 g/mol).

Suppose one has 1 mole of wheat bread slices (6.02×10$^{23}$ slices), referred to as "n" and the same number of white bread slices, referred to as "m," that gets converted to sandwiches. Mathematical relationships pertaining to the number of each kind of formed-sandwiches are described below.

$\varphi$=# of ways to select $k$ items from $w$=$w!/[k!(w-k)!]$ e.g. if w=9 and k=2, $\varphi$=(9×8×7×6×5×4×3×2×1)/(2!)(7×6×5×4×3×2×1)= (9×8)/2=36

If w is an extremely large number (such as 6.02×10$^{23}$) and k=2, for all practical purposes, $\varphi$=$w^2$/2

The total number of sandwich combinations = $\dfrac{[(n+m)!]}{k![((n+m)-k)!]}$ =

$\dfrac{\left[\dfrac{(6.02\times10^{23}+6.02\times10^{23})}{(6.02\times10^{23}+6.02\times10^{23}-1)}\right]}{2} = \dfrac{[(12.04\times10^{23})(12.04\times10^{23}-1)]}{2}$ $(\text{neglect}-1) = \dfrac{(12.04\times10^{23})^2}{2}$ $= 7.25\times10^{47}$ sandwiches $= \dfrac{(n+m)^2}{2}$ The probability (expressed as a decimal) of getting a wheat bread sandwich =

$\dfrac{[(n^2)/2]}{[(n+m)^2/2]} = \dfrac{[(6.02\times10^{23})^2/2]}{[(12.04\times10^{23})^2/2]} = \dfrac{(6.02\times10^{23})^2}{(12.04\times10^{23})^2} = 0.250$ The probability (expressed as a decimal) of getting a white bread sandwich =

$\dfrac{[(m^2)/2]}{[(n+m)^2/2]} = \dfrac{[(6.02\times10^{23})^2/2]}{[(12.04\times10^{23})^2/2]} = \dfrac{(6.02\times10^{23})^2}{(12.04\times10^{23})^2} = 0.250$ The probability (expressed as a decimal) of getting a sandwich with one slice of wheat bread and one slice of white bread = $(n\times m)/[(n+m)^2/2]$ =

$2mn/(n+m)^2 = \dfrac{[(2)(6.02\times10^{23})(6.02\times10^{23})]}{(6.02\times10^{23}+6.02\times10^{23})^2} = 0.500$ The same 0.500 answer can be obtained by using units of moles instead = $\dfrac{[(2)(1\text{ mole})(1\text{ mole})]}{(1\text{ mole}+1\text{ mole})^2} = 0.500$ These mathematical relationships can be applied to the analysis of molecules that are prone to dimerization and have most (over 80%) of the isotopic abundance coming from only one isotope, such as natural abundant GSH (over 80% of isotope abundance is from the 307.1 g/mol isotope) and isotopically enriched GSH (over 80% of abundance is from the 310.1 isotope). Let "n"=the µmol of natural abundant 307 g/mol GSH that became oxidized either to natural abundant 612 g/mol GSSG or "hybrid" 615 g/mol GSSG. Let "m"=the µmol of isotopically enriched 310 g/mol GSH that became oxidized to either "hybrid" 615 g/mol GSSG or fully enriched 618 g/mol GSSG. The ratio of the probability of getting "hybrid" 615 g/mol GSSG (sandwich with one slice of wheat bread and one slice of white bread) to the probability of getting fully enriched 618 g/mol GSSG (sandwich with two slices of white bread) equals the ratio of the peak areas from LC/MS/MS analysis of the peaks in the chromatogram representing those species of GSSG (after taking into account the abundances of those isotopes and subtracting out the contribution coming from natural abundant GSSG).

In positive mode ESI-MS, the most abundant isotope from natural abundant 612 g/mol GSSG is detected at 613 m/z, that from "hybrid" 615 g/mol GSSG with two $^{13}C$'s and one $^{15}N$ is detected at 616 m/z, that from enriched 616 g/mol GSSG with four $^{13}C$'s is detected at 617 m/z, and that from enriched 618 g/mol GSSG with four $^{13}C$'s and two $^{15}N$'s (which came from two 310 g/mol GSH's that each had two $^{13}C$'s and one $^{15}N$) is detected at 619 m/z. In positive mode electrospray tandem mass spectrometry (ESI-MS/MS) with the collision energy adjusted so as to make the most abundant product ion that which results from the loss of two pyroglutamates from GSSG (loss of 258 g/mol), the numbers above change to 355 m/z, 358 m/z, 359 m/z, and 361 m/z, respectively. The mathematical relationship described immediately following can be used to determine GSH and GSSG concentrations.

$$\frac{(358 \text{ m/z peak area})}{(361 \text{ m/z peak area})} =$$

$$\frac{(\text{probability of getting "hybrid" 615 g/mol } GSSG)}{(\text{that of getting 618 g/mol } GSSG)} =$$

$$\frac{[(2mn)/(n+m)^2]}{[(m^2)/(m+n)^2]} = 2n/m$$

$m = \mu$mol of 310 g/mol $GSH$ that became oxidized =

$(2 \times \mu$mol of 618 g/mol $GSSG$ present) +

($\mu$mol of 615 g/mol $GSSG$ present)

The mass of the solution of the enriched 310 g/mol GSH that was added is known, as is the mass and concentration of the enriched 616 g/mol GSSG solution. One can then determine the concentration (and, thus, μmol) of the 618 g/mol GSSG and 615 g/mol GSSG present by performing D-IDMS on both with the 616 g/mol GSSG representing the enriched analyte. One μmol of 618 g/mol GSSG comes from two μmols of 310 g/mol GSH, and one μmol of 615 g/mol GSSG comes from one μmol each of 307 g/mol GSH and 310 g/mol GSH. Using this relationship, one can determine "m" (the μmol of 310 g/mol GSH that became oxidized). Once "m" is known, one can determine "n" (the μmol of natural abundant 307 g/mol GSH that converted to either 612 g/mol GSSG or 615 g/mol GSSG) using the following relationship:

[(358 m/z peak area)/((361 m/z peak area)*(2))]
\*$m=n=$μmol of 307 g/mol GSH that became oxidized Since the mass of the sample (e.g. blood sample, plasma sample, etc.) is known, one can determine the concentration of GSH that became oxidized to GSSG in units such as μmol/g (and, subsequently, μg/g) or smaller quantities, and perform the necessary subtraction from the uncorrected GSSG concentration and the necessary addition to the uncorrected GSH concentration.

The D-SIDMS analyses of the glutathione and its speciated compounds were conducted on red blood cells, serum and plasma of children with ASD and control children. This is one example of the diagnostic abilities and statistical validation of the Glutathione Assay when measured as a suite of compounds with corrections of inter-species transformations and conjugated forms provided by D-SIDMS.

Prior art associated with the measurement of GSH and its sub-compounds and conjugates is in agreement that this type of measurement is not possible with the currently available tools, methods or technologies. This invention overcomes these limitations by novel application of D-SIDMS and mathematical, algorithmic derivation of analyte concentrations using isotopic properties.

Referring now to FIG. 2, the average red blood cell total glutathione concentrations in children with autism and controls. The p value is 0.011 with n=27 pairs. The significance is that this demonstrates that the higher accuracy measurement is statistically significant as a biomarker.

In FIG. 3 the total glutathione reduced GSH is also a statistically significant biomarker for diagnosing and evaluation of children with autism and undergoing treatment and is sensitive for trends and changes and responses during treatments. The control children show a statistically significant difference from the children with autism.

In FIG. 4. the importance of the relationship between sub-species of glutathione are demonstrated as products and relationships of sub-components of glutathione are statistically significant and without sub-components there would be no opportunity to either measure these species accurately or to derive the significance of form the sub-species relationships.

In FIGS. 5 and 6, Glutathione Logistic Regression Results have been prepared that demonstrate the capability to use glutathione sub-species for predicting this disease. These logistic regression analysis of glutathione concentrations which were performed take into account the regional prevalence of autism between 1 and 3 percent. The significant results are shown in the figures relating glutathione concentrations to autism diagnostic percentage and also demonstrate the significance as a biomarker and diagnostic tool.

In practice, both drugs and toxins form conjugates with glutathione and have been measured as demonstrated in FIGS. 7a-7b. The conjugates of glutathione with methyl mercury and ethylmercury and inorganic mercury appear as clustered peaks in FIGS. 7a-7b.

In FIG. 8, the GSH and GSSG ratio of identical twin girls having ages of less than eight years old were diagnosed to have ASD. The twin on the left had a statistically significant increase in the GSH/GSSG ratio after correction for GSH to GSSG oxidation in the testing procedure. The twin on the right after the same treatment did not have show the improvement and indeed was reported medically not to have improved. These data demonstrate that the GSH/GSSG or zeta to gamma ratio is effective at diagnosing immune function and changes in the condition of the patient.

It is also possible to quantify glutathione species according to the invention for the purpose of tracking and quantifying heavy metal toxins with which glutathione forms complexes. In other words, diagnostic levels of tGSH, GSH and the GSH/GSSG ratio can be assessed and then correlated to GSH-conjugates containing heavy metals and their conjugates, wherein such heavy metals may be, without limitation, methylmercury, inorganic mercury, cadmium, selenium, and lead. One skilled in the art who learns from the present invention how to measure, calculate and quantify glutathione and glutathione species will be able to practice the invention to track and to quantify heavy metals by extension.

Although the invention has been described herein with particularity, the invention is only to be limited insofar as is set forth in the accompanying claims.

The invention claimed is:

1. A method of assessing wellness or diagnosing illness including autism and chronic fatigue syndrome in an human patient in need of such diagnosis, by performing a laboratory assay, said assay comprising the steps of:
   a) adding to a sample collection container all three of 1) isotopically enriched glutathione (GSH), 2) isotopically enriched glutathione disulfide (GSSG) and 3) a measured amount of a thiol-group blocking agent; followed by
   b) adding to said sample collection container of step a) a patient sample of blood, urine, saliva, blood components or tissue; wherein said thiol-group blocking agent forms a conjugate with all GSH present in the sample, said conjugate's significantly reducing but not stopping the oxidation or transformation of said GSH in said conjugate;

c) assaying said patient sample for the ratio of GSH and glutathione disulfide (GSSG) originally present in said sample at the time of collection and correcting the assayed ratio for oxidation or transformation of said GSH by direct IDMS (D-IDMS) accounting for species' transformations and conjugates and direct speciated isotope dilution mass spectrometry by calculating transitions based on the behavior of said isotopically enriched GSH and said isotopically enriched GSSG; and c) reporting and determining the corrected ratio of said GSH to said GSSG original to said sample, such that if the ratio of GSH to GSSG in said patient sample is between 15-200, said ratio is indicative of illness including vulnerability to autism or chronic fatigue syndrome.

2. The method according to claim 1, wherein said thiol-group blocking agent is NEM.

* * * * *